United States Patent [19]

Good et al.

[11] Patent Number: 4,886,782
[45] Date of Patent: Dec. 12, 1989

[54] MALARIAL IMMUNOGEN

[75] Inventors: Michael A. Good, Rockville; Jay Berzofsky, Bethesda; Louis H. Miller, Chevy Chase, all of Md.

[73] Assignee: The United States of America as represented by the Department of Health and Human Services, Washington, D.C.

[21] Appl. No.: 19,000

[22] Filed: Feb. 26, 1987

[51] Int. Cl.$^4$ .................. A61K 39/12; C07K 7/08; C07K 7/10
[52] U.S. Cl. .................. 514/12; 514/13; 514/895; 530/326; 530/324; 424/88; 424/89
[58] Field of Search .................. 530/351, 326, 324; 424/85, 89, 88; 514/12, 13

[56] References Cited

PUBLICATIONS

Gibson et al., Proc. Nat'l. Acad., Sci. USA 83, 5649–5653(1986).
Good et al., J. Exper. Med. 164:655–660 "Genetic Control of the Immune Response in Mice to a *Plasmodium falciparum* Sporozoite Vaccine", 1986.
Dame et al., Science 225:593–599, "Structure of the Gene Encoding the Immunodominant Surface Antigen on the Sporozoite . . .", 1984.
Miller et al., Science 234:1349–1356, "Research Toward Malaria Vaccines", 1986.
Chen et al., J. of Immun. 118:1322–1327, "Immunity to Sporozoite–Induced Malaria Infection in Mice", 1977.
Mazier et al., Science 213:156–159, "Effect of Antibodies to Recombinant and Synthetic Peptides on *P. falciparum* Sporozoites in Vitro", 1986.

*Primary Examiner*—Margaret Moskowitz
*Assistant Examiner*—F. T. Moezie
*Attorney, Agent, or Firm*—Mishrilal Jain

[57] ABSTRACT

The circumsporozoite (CS) protein of *Plasmodium falciparum* has been analyzed to develop a new anti-sporozoite malarial vaccine. Localization of sites for T-cell recognition on this molecule is critical for vaccine design. By using an algorithm designed to predict T-cell sites and a large panel of H-2 congenic mice, a major nonrepetitive T-cell was located. When a synthetic peptide corresponding to this site was covalently linked to the major B-cell site on the molecule, an immunogen capable of eliciting a high titer antibody response was formed. This peptide sequence is capable of priming helper T-cells for a secondary response to the intact CS protein. This site represents the first helper T-cell site described for the CS molecule outside of the repetitive region, and is a major immunodominant T-site on the molecule. The approach described herein is useful in the rational design and construction of more efficacious vaccines.

7 Claims, 4 Drawing Sheets

```
                    10                      20                        30
M M R K L A I L S V S S F L F V E A L F Q E Y Q C Y G S S S
    1 1 1 1 1 0 0 0 0 0 0 0 0 0 0 0 0 0 0 1 0 0 0 0 0

40                      50                        60
N T R V L N E L N Y D N A G T N L Y N E L M N Y Y G K Q E
1 0 1 1 1 1 1 1 1 0 0 0 0 1 1 1 1 1 0 0 1 0 0 0 0 0 1 1 0 0

70                      80                        90
N W Y S L K K N S R S L G E N D D G N N N G D N G R E G K
1 1 0 0 1 0 0 0 1 1 0 0 0 0 0 0 0 0 0 0 0 1 0 1 1 1 1 1 0 0

100                     110                       120
D E D K R D G N N E D N E K L R K P K H K K L K Q P G D G N
0 0 0 0 0 0 0 0 0 0 0 0 0 0 0 0 1 1 1 0 1 1 1 1 1 0 0 0

130                     140                       150
P D P N A N P N V K P N A N P N V D P N A N P N V D P N A N
0 0 0 0 0 0 0 0 0 0 0 0 0 0 0 0 0 0 0 0 0 0 0 0 0 0 0 0 0 0

155        REPEAT          281                      290
P N A N P ................. A N P N A N P N K N N Q G N G
0 0 0 0 0 ................. 0 0 0 0 0 0 0 0 0 0 0 0 0 0

MALARIAL IMMUNOGEN

BACKGROUND OF THE INVENTION

The present invention is related generally to malarial vaccines. More particularly, the present invention is related to a synthetic peptide stimulating T cell immunity to malaria circumsporozite protein and an improved method for rational design of new synthetic or recombinant fragment vaccine.

State of the Art

Lately, vaccine development as a possible means of preventing malaria has received much attention. The Malaria parasite (Plasmodium species) is carried by mosquitoes that inoculate the mammalian host with sporozoites. The sporozoites travel to the liver and commence the excoerythrocytic stage of their life cycle. If they could be blocked before they entered hepatocytes, or if the infected hepatocytes could be destroyed prior to rupture and liberation of merozoites, the disease would be prevented.

Sporozoite-blocking vaccines currently being tested in humans consist of malaria repeated epitope of the circumsporozoite (CS) protein convalently linked to sequence unrelated to the parasite. This construction is based on the observations that: (a) the central third of the CS protein contains a tandemly repeated epitope that does not differ among the various isolates tested Dame, et al, Science 225, 593 (1984); Weber et al, Molec. Biochem. Parasitol 15, 3054, 1985 and (b) antibodies to this epitope can prevent invasion of hepatocytes in vitro, (Young et al, Science 228, 958 (1985); Zavala, et al, Science 228, 1436, 1985); and protect mice in vitro from challenge with murine malaria (P.Berghei), Potocniak, et al, J. Exp. Med. 151, 1504 (1980).

Recently the immune response in mice to one of these vaccines, which is referred to as R32tet$_{32}$ was examined. It is produced as a fusion protein between 32 tandem repeats [(NANP)$_{15}$NVDP]$_2$ (single letter amino acid code) derived from the CS protein and part of a sequence (32 residues) encoded by a tetracycline resistance gene read out of frame, (Young, et al, Science 228, 958 1095). It was shown, (Good, et al, J. Exp. Med. 164, 655, 1986), that only mice carrying the I-A$^b$ gene could produce a T-cell response to the malaria-encoded sequence (NANP)$_n$, a finding that has been confirmed by other workers, (Guidice, et al, J. Immunol. 137, 2952, 1986). In such mice, (NANP)$_n$ stimulated proliferating T-cells as well as helper T-cells. The tet$_{32}$ peptide also contained a T-cell site (or sites) but was recognized after immunization with R32tet$_{32}$ by only two of seven congenic mouse strains that differed only at their H-2 loci. If a similar situation occured in humans, some would not respond to the vaccine. Thus, despite attempts, a vaccine producing more effective immunity against malaria in a larger population is still needed.

SUMMARY OF THE INVENTION

It is, therefore, an object of the present invention to provide a new synthetic peptide which, when administered to a host suseptible to malaria infection, is capable of inducing protective immunity against malaria.

It is a further object of the present invention to provide a synthetic peptide capable of stimulating T-cell proliferation and increased production of antibodies against malaria circumsporozoite protein.

It is yet another object of the present invention to provide an improved method for rational design of new synthetic or recombinant fragment vaccine.

Various other objects and advantages would become apparent from the Detailed Description of the Invention.

BRIEF DESCRIPTION OF DRAWINGS

These and other objects, features and many of the attendant advantages of the invention will be better understood upon a reading of the following detailed description when considered in connection with the accompanying draings wherein:

FIG. 1 shows the amino acid sequence of CS protein of the 7GB strain of P. falciparum as analysed for helical amphipathic segments by AMPHI. One (1) indicates the center of an 11-residue block with periodicity of hydrophobicity like that of an amphipathic $\alpha$ or 3$_{10}$-helix. Zero (0) indicates the center of blocks with other periodicities.

Figure 2:
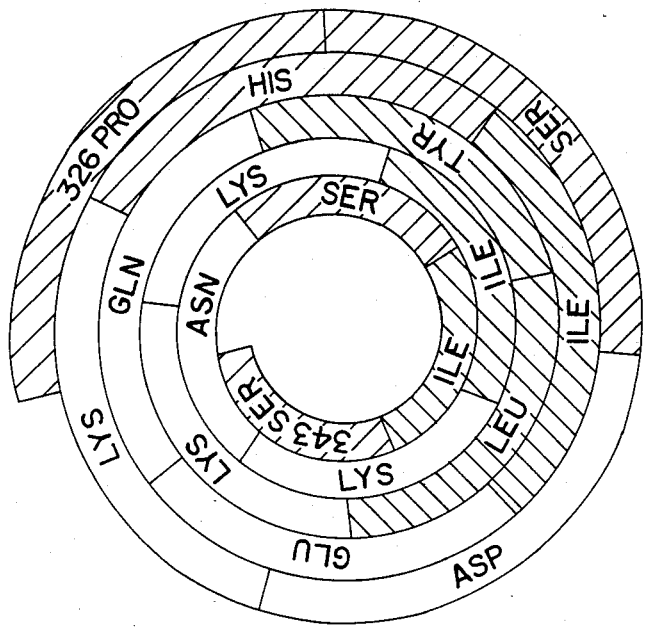
FIG. 2 is a spiral diagram of CS protein 326(P) to 343(S), showing $\alpha$-helical amphipathicity. View is looking down the helix from the N-terminal. Darkly shaded area represent hydrophobic residues, stippled areas represent neutral residues, and open areas represent hydrophobic residues. The serparation of hydrophobic and hydrophilic residues on opposite sides of the helix constitutes amphipathicity.

Anti-(NANP)$_n$ Ig was determined for pooled sera taken on day 20 (open symbols) and day 31 (closed symbols) by ELISA.

DETAILED DESCRIPTION OF THE INVENTION

The above and various other objects and advantages of the present invention are achieved by synthetic peptides having at least a T-cell site with or without the addition of another antigenic site. Two such peptides from the CS protein having in whole or in part the following amino acid sequences in terms of the conventional single letter code, are now exemplified:

(1) PSDKHIEQYLKKIKNSIS
(2) PSDKHIEQYLKKIKNSIS(C)-NP(NANP)-5NA, wherein (C) represents cysteine at carboxy terminus. The sequence: PSDKHIEQYLKKIKNSIS(C) is abbreviated Th2R.

Unless defined otherwise, all technical and scientific terms used herein have the same meaning as commonly understood by one of ordinary skill in the art to which this invention belongs. Although any method and material similar or equivalent to those described herein can be used in the practice or testing of the present invention, the preferred methods and materials are now described. All publications metioned hereunder are incorporated herein by reference.

Of course, having described the amino acid sequence of the polypeptide of the present invention, such polypeptides can be routinely synthesized by standard techniques well known in the art, such as by commercially available peptide synthesizers and the like. Such standard techniques of poplypeptide synthesis can be found described in such publications as Merrifield, *J. Chem, Soc.* 85:2149–2154, 1963; Hunkapillar et al, *Nature* 310: 105–111, 1984.

It is noted, however, that the amino acid sequence of the polypeptide as recited herein above, shows only essential portions required for immunogenic activity. In otherwords, the polypeptide is not limited to the minimal sequences shown above, but must have, at least in part, the amino acid sequence shown above. Of course, various analogs and derivatives of the polypeptide of the present invention can be easily predicted, generated and/or prepared by such standard and common methods as NMR (Nuclear magnetic resonance), computer modeling and the like and all such analogs or derivatived which are equivalent in structure and function to the polypeptides as defined herein are encompassed within the scope of the disclsoure contained herein.

Indeed, the polypeptides of the present invention are arrived at by the use of computerized program to generate an algorithm which could predict T-cell epitope(s) on the CS protein. The method comprises (a) first identifying by using a computerized algorithm T-cell epitopes on a protein against which an immunogen is to be designed; (b) then synthesizing said T-cell epitopes; (c) then testing the synthesized T-cell epitopes for antibody production in a model host; (d) then conjugating one or more antobody producing T-cell eiptope determined from step (c) with a B-cell epitpoic sequence and recovering desired synthetic immunogen.

When the CS protein of *P. falciparum* was searched through the uniquely developed algorithm, certain T-cell epitopes were recognized which posses the desired characteristics of amphipathicity. It was then discovered that a potential T-cell epitopic major site on the CS protein occurred in a region located about 40 amino acids from the tandem repeats, toward the carboxyl terminus, representing amino acids 326 to 343 (see FIGS. 1 and 2).

Figure 5:
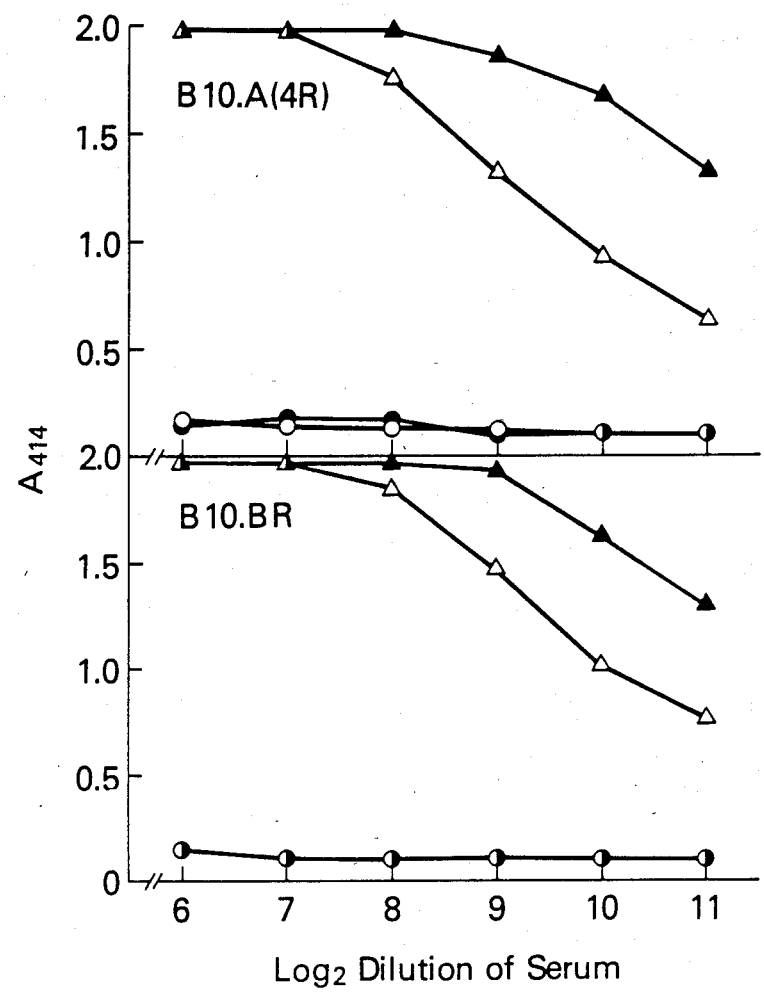
FIG. 5 shows the result when B10.BR and B10.A(4R) mice (five per group) were immunized intraperitoneally with 100 $\mu$g of the conjugate Th2R-NP(NANP)$_5$NA emlusified in CFA (△,▲) or with 100 $\mu$g of NP(NANP)$_5$NA emulsified in CFA (○, ●) on day 0 and boosted on day 21 with aqueous antigen (30 $\mu$g).

A peptide corresponding to this region elicited an immune response in the same congenic strains that gave the optimal response to the entire CS protein [B10.BR, B10.A(4R)]. It was further established that this peptide was a helper T-cell site by covalently linking it to the sequence, NP(NANP)$_5$NA. This construct elicited high titers of antibodies in those congenic strains [B10.,BR and B10.A(4R)] that did not respond to the repeated tetrapeptide sequence alone (FIG. 5).

Although any conventional technique well known in the art for preparing an amino acid conjugate can be employed, the following procedure was used herein to make the TH2R-NP(NANP)$_5$ NA conjugate 5.7 mg of m-maleimidobenzoyl-N-hydroxysuccinimide ester (MBS) (Peirce Chemicals) in 380 ul of dimethlyformamide was added dropwise to 15 mg of NP(NANP)$_5$NA in 1.5 ml of 10 mM NaPO$_4$, pH 7.0. The mixture was stirred for 30 minutes at room temperature (about 22° C.–27° C.) and then the m-maleimidobenzoyl peptide (MB-peptide) was separated from the unreacted MBS by desalting on a column of sephadex G-25 in 50 mM PO$_4$, pH 6.0. The resulting MB-peptide pool mixed with 15 mg of the TH2R peptide in 15 ml of phosphate buffered for 3 hours. The final Th2R-NP(NANP)$_5$NA conjugate was desalted on a column of Bio Gel P-2 (Bio-Rad) and analyzed by reversed phase HPLC and amino acid composition.

To determine whether there were T-cell sites other than the NANP repeat on the CS protein, various congenic strains of mice were immunized with an infectious recombinant vaccinia virus encoding the entire CS protein from the 7G8 srain of *P. falciparum,* (Dame, et al, *Science* 225, 593, 1984); and the antibody resonse to (NANP)$_n$ was monitored; said recombinant vacciniavirus being referred herein as CS-vaccinia virus. As shown in Table 1 it was found that not only did the B10 (H-2$^b$) strain respond to CS-vaccinia virus as expected, since mice carrying the I-A$^b$ gene have been known to make anti-(NANP)$_n$ antibodies following immunization with (NANP)$_n$, but B10.BR and B10.A(4R) mice, whose T-cells do not respond to (NANP)$_n$, also produce antibodies to the repeat sequence. The other strains examined responded less well. Control experiments showed that no mouse strain tested produced antibodies to (NANP)$_n$ after inoculation with the parent vaccinia virus. As further control, all mice responded comparably to parent vaccinia virus. These data indicated that there must be one or more helper T-cell sites, apart from (NANP)$_n$, located on the CS protein, that can be recognized by B10.BR and B10.A(4R) mice. However, if there were many T-cell sites located on the CS protein, many if not most of the different strains of mice would respond well to the CS-vaccinia virus which expressed the entire CS protein. Because many strains did not respond it was hypothesized that there were only a limited number, if at all, of other major helper T-cell sites.

The fact that both the B10.BR mice, which express both I-A and I-E molecules (I-A$^k$, I-E$^k$) and the B10.A(4R) mice which express only I-A molecules (I-A$^k$) respond, suggests that this T-Cell site is recognized in association with I-A$^k$. The possibility exists, however, that the B10.BR strain recognizes two T sites, one in association with I-A$^k$ and one in association with I-E$^k$.

To search for candidate helper T-cell sites that might be recognized by the I-A$^k$-bearing strains of mice, advantage was taken of the observation that immunodominant helper T-cell sites tend to have the ability to fold as amphipathic helices, (Spouge, et al, *J. Immunol.* 138, 204, 1987); and are frequently near the B-cell site, (Berzofsky, *Surv. Immunol. Res.* 2, 223 (1983); Manca et al, *Eur. J. Immunol.* 15, 345, 1985). Using the computer algorithm, the sequence of the CS protein was analyzed by a least squares fit of a sine wave to the hydrophobicity values of the amino acids along the sequence to find those segments that could best fold as amphipathic α or 3$_{10}$-helices. The analysis (FIG. 1) indicated that a segment from residues 323 to 349 had the highest amphipathic score in the whole protein (Table 2). Because a high amphipathic score may be indicative of a T-cell site, this segment was used as a candidate for an immunodominant T-cell epitope. The amphipathic character of this sequence becomes apparent when viewed as a helix in a spiral diagram (FIG. 2). The region 103 to 122 (Corresponding to blocks with midpoints 108 to 117) would be amphipathic if folded as a 3$_{10}$ -helix, although the amphipathic score is lower. Because the sequence 103 to 116 has been made for other purposes, it was tested for its ability to stimulate T-cells as well. Both sequences 323 to 349 and 103 to 116 have the advantage of being close to the B-cell (NANP)$_n$. The block from 298 to 309 also meets these criteria but contains two closely spaced helix breaking prolines; hence it was not tested. The repeat region (NANP)$_n$ would not be predicted to form an amphipathic α or 3$_{10}$-helix, although it could possibly fold as an amphipathic α structure (periodicity of 2 or frequency 180°).

TABLE 1

Genetic control of immune response to *P. falciparum* CS protein.
The results are shown as the titer of antibodies to (NANP)$_n$. Mice (five per group) were immunized intraperitoneally on day 0 and by scarification on day 21 with the CS-recombinant vaccinia (without adjuvant). Serum samples for the 1° primary response were taken on day 20 and for the secondary response on day 35; the samples for each response were pooled prior to assay. All sera were assayed on the same day.

| Strain | \multicolumn{8}{c}{H-2 alleles} | | | | | | | | Primary response | Secondary response |
|---|---|---|---|---|---|---|---|---|---|---|
| | K | A | B | J | E | C | S | D | | |
| B10 | b | b | b | b | (b) | b | b | b | 79 | 111 |
| B10.BR | k | k | k | k | k | k | k | k | 79 | 274 |
| B10.A(4R) | k | k | b | b | (b) | b | b | b | 69 | 630 |
| B10.S(9R) | s | s | s | k | k | d | d | d | <<16 | 60 |
| B10.S(7R) | s | s | s | s | (s) | s | s | d | <<16 | 34 |
| B10.D2 | d | d | d | d | d | d | d | d | <16 | 16 |
| B10.M | f | f | f | f | f | f | f | f | <16 | 39 |
| B10.Q | q | q | q | q | q | q | q | q | <<16 | <<16 |
| B10.RIII | r | r | r | r | r | r | r | r | <<16 | <16 |

The titer is defined to be the dilution of serum giving an absorbance (414 nm) of 0.5 in an ELISA assay. This definition was chosen to facilitate comparison of sera, but by a more conventional definition of titer as the highest dilution giving an absorbance significantly greater than a panel of normal mouse sera, the titers would be all numerically higher. The antigen used to coat the ELISA plates was R32tet$_{32}$.

TABLE 2

| The predicted amphipathic segments, angles, and amphipathic scores (AS) in the CS protein of *P. falciparum*. | | |
|---|---|---|
| Midpoints of blocks | Range of angles | AS |
| 6–10 | 130–135 | 7.4 |
| 33–39 | 110–130 | 14.0 |
| 44–48 | 90–120 | 12.0 |
| 69–70 | 95–100 | 4.8 |
| 83–88 | 120–100 | 19.5 |
| *108–111 | 135—135 | 7.4 |
| *113–117 | 115–135 | 12.5 |
| 298–309 | 85–110 | 32.9 |
| *328–344 | 80–100 | 43.5 |
| 365–369 | 95–135 | 9.2 |
| 379–383 | 80–100 | 9.8 |
| 385–397 | 95–130 | 30.7 |

*Regions tested in vivo

Based on the observations noted herein above, the synthetic peptide sequences (103 to 116, 107 to 124, and 326 to 343, C) were made and tested for their ability to prime helper T-cells. Mice were primed by intraperitoneal injections with peptide emulsified in complete Freund's adjuvant (CFA) or with saline emulsified with CFA (five mice per group). Six weeks later, the mice were infected with CS-vaccinia virus by scarification in the base of the tail. Nine days later, their sera were tested by standard enzyme-linked immunoadsorbent assay (ELISA). The ELISA was performed as follows. Immulon-1 microtiter plates (Dynatek, Alexandria, Va.) were coated with R32tet$_{32}$ (obtained from Smith Kline and French Lab), 100 ul per well at a concentration of 2 μg.ml. The plates were washed and the sera diluted in phosphate buffered saline pH 7.4 containing 1% bovine serum albumin (BSA) and 0.05% Tween 20. After incubation for 1 hour at 37° C. followed by washings, horseradish peroxidase conjugated goat-antiserum to mouse Ig was added. The plates were incubated again for 1H at 37° C., washed and substrate added. The substrate was 2,2'-azino-di (3-ethylbenzthiazoline sulfonate), ABTS). The reaction was stopped by the addition of 1.25% KI. Optical density was read at 414 nM with a flow Titertek Multiskan.

Figure 3:
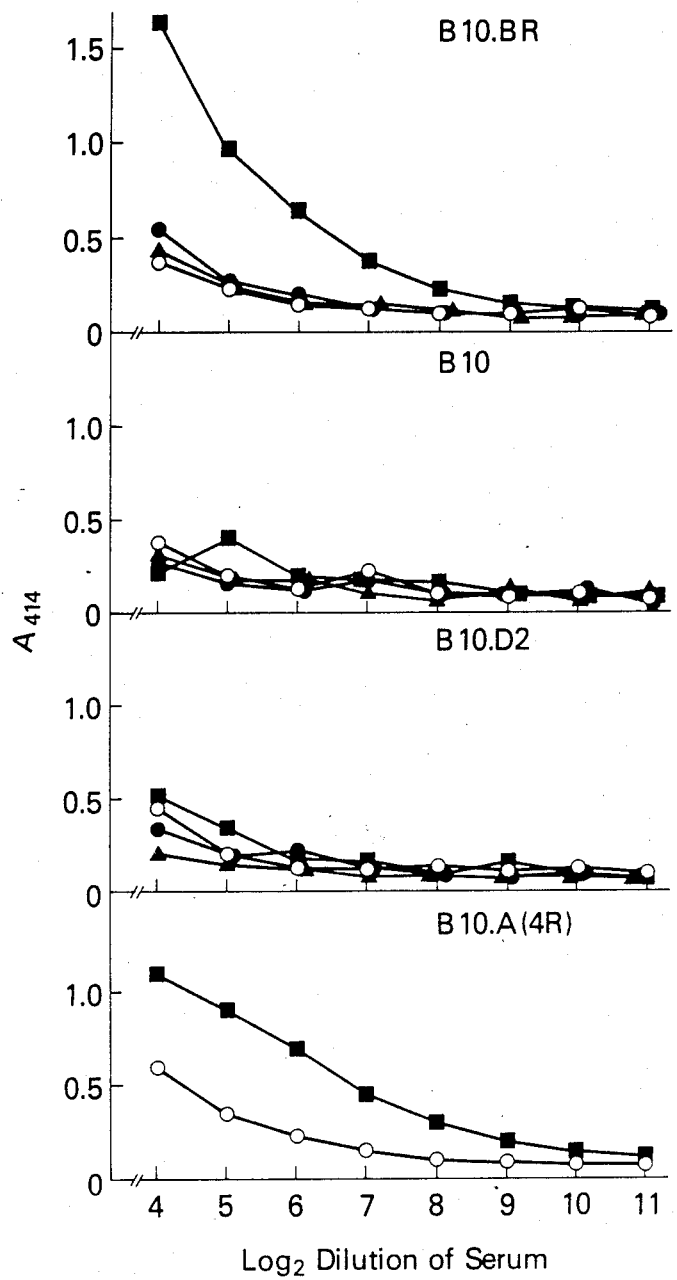
FIGS. 3 shows the result when B10.BR, B10, B10.D2 and B10.A(4R) mice (five per group) were immunized with peptide (100 $\mu$g) emulsified in CFA, and five weeks later they were challenged with the CS-vaccinia virus by scarification. Nine days after challenge, sera were collected and antibodies to (NANP)$_n$ were measured in the pooled sera from each group. The peptides used for the immunization were as follows: ■, Th2R [PSDKHIEQYLKKIKNSIS(C)], representing amino acids 326 to 343 from the sequence of CS protein from the 7G8 strain of P. falciparum, plus an extra cysteine at the COOH terminus; ▲ EKLRKPKHKKLKQP, representing amino acids 103 to 116; ●, KPKHKKLKQPGDGNPDPN, representing amino acids 107 to 124; o, saline. The B10.A(4R) mice were tested only with the Th2R tomap the genetic regulation of the positive response in B10.BR mice (see also Table 1).

As shown in FIG. 3, B10.BR or B10.A(4R) mice primed with peptide sequence 326 to 343, C/CFA produced significantly more antibody to (NANP)$_n$ after challenge with CSA-vaccinia virus than did the control mice primed with saline/CFA. At later time points after challenge, the titers of all the antibodies increased, but the control mice developed a significant primary response to the CS-vaccinia challenge, making comparison more difficult. This T-cell site (peptide 326 to 343) which has been designated herein as Th2R, is the second region of the CS molecule found to contain a helper T-cell site. Other piptide sequences did not prime helper T-cells in these strains. Because Th2R does not include the NANP sequence, the difference in the antibody response specific for (NANP)$_n$ between the two groups was due to T-cell priming. The CS protein encoded by the recombinant virus contains both the B cell site [(NANP)$_n$] and the T-cell site (Th2R] linked on the same molecule, and therefore prior immunization with Th2R can enhance specific help to the B-cells that recognise (NANP)$_n$. B10 strain mice did not respond to Th2R, and did not produce a secondary response 9 days after challenge with CS-vaccinia virus. To confirm that all of these mice contained B cells capable of recognizing (NANP)$_n$, it was shown that they could produce antibodies to (NANP) after vaccination with keyhole limpet hemocyanain (KLH) conjugated to (NANP)$_n$. This is not unexpected, since the strains differ only at their H-2 loci—a region influencing T-cell recognition of antigen and indirectly the antibody responses but not affecting the immunoglobulin structural gene repertoire of B-cells.

Figure 4:
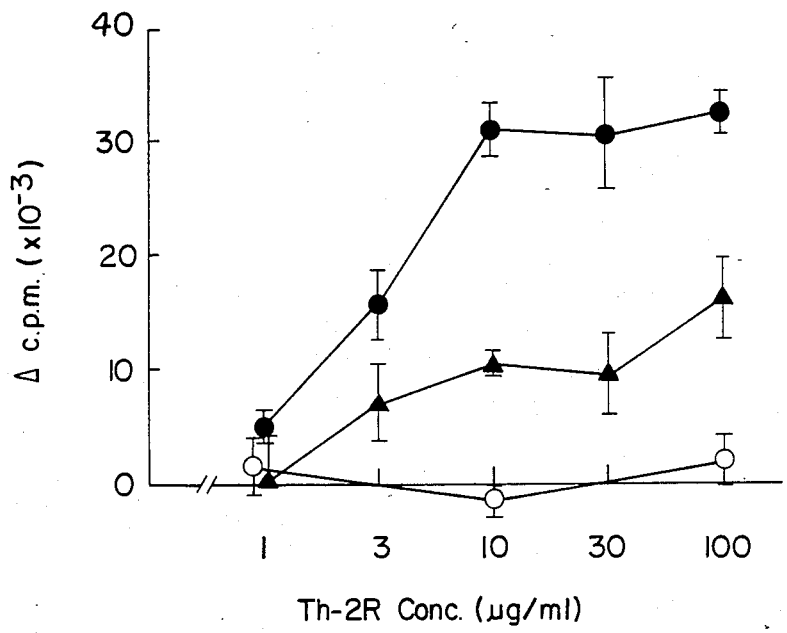
FIG. 4 shows the results when B10.BR (▲), B10.A(4R)(●) and B10(○) mice (2 per group) were immunized subcutaneously in the base of the tail with 100 $\mu$g of Th2R [PSDKHIEQYLKKIKNSIS(C)] emulsified in CFA. Ten days later, draining lymph node cells (4×10$^5$ per 0.2 ml, quadruplicate) were challenged in vitro (RMI, 10% heat-inactivated fetal calf serum, 5×10$^{-5}$M 2-mercaptoethanol) with different concentrations of Th2R and proliferation was assessed four days later determining incorporation of $^3$H-thymidine (New England Nuclear, 6.7 Ci/mmole) during a 16 hour pulse (1 $\mu$Ci/well). Background radioactivity (no antigen in vitro) was 24,232 c.p.m. for B10.BR and 21,387 c.p.m. for B10.A(4R) and 16,653 c.p.m. for B10. Vertical bars represent +/− one standard error of the mean.

To determine if Th2R was recognized by proliferating T-cells, a lymph node cell transformation assay was performed, as described by Corradin, et al, *J. Immunol.* 119, 1048, (1977) in B10.A(4R), B10.BR, and B10 mice. The peptide was used as both immunogen and antigen. As shown by the results in FIG. 4, proliferating T cells from both B10.A(4R) and B10.BR mice recognized the sequence. It was consistently found that the B10.A(4R) response to Th2R was greater than the B10.BR response. As a control for possible mitogenic effects of Th2R, it was shown that the Th2R did not stimulate a proliferative response in lymph node cells from immunized B10 mice. The sequence 103 to 116, while not stimulating T-cell help, could stimulate T-cell proliferation. Thus, while not all proliferating T-cells are necessarily helper T-cells, the proliferative response to Th2R can be correlated with priming for help to CS-vaccinia virus.

Based on the observations noted above, a new cojugate synthetic immunogen containing both the T-cell and the B-cell sites derived from the Cs molecule was constructed. This conjugate, namely, Th2R-NP(NANP)$_5$ NA or NP(NANP)$_5$NA was used to immunize B10.BR and B10.A(4R) mice and the antibody production measured. Both mice strains responded to the conjugate peptide but not to NP(NANP)$_5$NA alone (FIG. 5). In the native molecule, the NANP repeating unit is located between Th2R and the NH$_2$ terminus, whereas in the synthetic construct, NP(NANP)$_5$ NA was located at the carboxyl terminal end of Th2R. This change in orientation did not affect the ability of the T-cell site to generate carrier specific help for the responsive B-cells. Thus, a synthetic immunogen was designed and constructed containing a T-cell site and a B-cell site, both of parasite origin, for an antimalaria vaccine.

While the CS protein appears to contain few major epitopes capable of stimulating T-cells to help an anti-(NANP)$_n$ B-cell response, it may contain other epitopes responsible for T-cell proliferation which may be important for antibody-independent cellular immunity. As mentioned, peptide 103 to 116 may represent such an epitope. It may also contain other sites recognized by cytotoxic T-cells which may play a role in sporozoite immunity. While the specific helper T-cell epitope (Th2R) for an anti-(NANP)$_n$ B-cell response has been shown efficacious herein, other helper T-cell epitopes may of course be present which may preferentially help B-cells of other specificities; however, the anti-(NANP)$_n$ Ig specificity is the one known to neutralize sporozites. T-cell sites are required both for helper function in antibody production and for antibody-independent cellular immunity, both of which appear to be important in immunity to sporozoites.

A vaccine to be used in endemic areas would rely on natural boosting by sporozoites is required, or if antibody-independent T-cell immunity is critical, a vaccine must contain parasite-derived T-cell epitopes as the results presented herein indicate. Natural boosting by sporozoites would maintain a high antibody titer, known to be necessary for antibody-mediated protection, as well as maintain T-cells in an activated state; however, if T-cell sites are limited on the CS molecule, a vaccine reliant on natural boosting may be ineffective in some people. The data obtained herein indicate that the more T-cell sites are incorporated in a vaccine, the more this problem can be minimised. The approach described herein now provides a new tool in the rational design of synthetic or recombinant fragment vaccines.

Of course, pharmacetical compositions such as vaccines, comprising the conjugated polypeptide of the present invention as an active ingredient in an amount sufficient to produce immunogenic effect in susceptible host and a pharmaceutically acceptable, non-toxic sterile carrier can be easily prepared based on the data provided herein. Such carriers could be fillers, non-toxic buffers, physiological saline solution and the like. The preparation can be used systemically and may be in any suitable form. Of course, the covalently linked poplypeptide of the present invention may also be administered in combination with other adjuvants, protease inhibitors, or compatible drugs where such combination is seen desirable or advantageous in controlling malarial infection.

Of course, the response to a vaccine requires T-cell help and to elicit natural boosting, the vaccine must contain malaria-derived T-epitopes. If the region which stimulated protective antibodies contains only one T-epitope, it will be seen by only a limited segment of the population. The present invention located the major T-cell epitope on the circumsporozoite protein. This peptide elicits T-cell immunity and, when coupled to any other antigenic site such as the repetitive region, elicits antibodies in those subjects which do not respond to the repeat alone. Used either alone or coupled to other malaria-derived antigenic sequences, the T-cell epitope of the present invention, can provide an antimalarial vaccine with longer lasting immunity to a broader segment of the human population than possible by the currently developed malarial vaccine.

It is understood that the examples and embodiments described herein are for illustrative purposed only and that various modifications or changes in light thereof will be suggested to persons skilled in the art and are to be included within the spirit and purview of this application and the scope of the appended claims.

What is claimed is:

1. A polypeptide consisting essentially of a T-cell epitope of the circumsporozoite protein of *P. falciparum*, said polypeptide having the following amino acid sequence in terms of single letter code: PSDKHIEQYLKKIKNSIS.

2. A polypeptide consisting essentially of a T-cell epitope of the CS protein of *P. falciparum* having an amino acid sequence, in terms of single letter code, of PSDKHIEQYLKKIKNSISC, covalently linked to NP(NANP)$_5$NA at the C residue, wherein C represents a cysteine at the carboxy terminus of said polypeptide.

3. A pharmaceutical composition comprising the polypeptide of claim 1 in an amount sufficient to stimulate an immune response in a host to the circumsporozoite protein of *Plasmodium falciparum*, and a pharmaceutically acceptable carrier.

4. A pharmaceutical composition, comprising the polypeptide of claim 2 in an amount sufficient to stimulate an immune response in a host to the circumsporozoite protein of *P. falciparum*, and a pharmaceutically acceptable carrier.

5. A method for inducing immunity against *P. falciparum* malarial infection in a susceptible host comprising administering to a host susceptible to *P. falciparum* infection an immunizing amount of the polypeptide of claim 1.

6. A method for stimulating T-cell immunity against circumsporozoite protein, comprising administering to a host susceptible to to infection by *P. falciparum* a T-cell proliferating amount of the polypeptide of claim 2.

7. A method for inducing immunity against *P. falciparum* malarial infection in a susceptible host, comprising administering to a host susceptible to *P. falciparum* infection an immunizing amount of the polypeptide of claim 2.

* * * * *